United States Patent [19]

Tsukamoto et al.

[11] 4,232,010
[45] Nov. 4, 1980

[54] CALCIUM-ANTAGONISTIC COMPOSITION

[75] Inventors: Goro Tsukamoto, Toyonaka; Koichiro Yoshino, Osaka; Tominori Morita, Nishinomiya; Takashi Nose, Suita; Mitsuo Okazaki, Tama, all of Japan

[73] Assignee: Kanebo, Ltd., Tokyo, Japan

[21] Appl. No.: 39,311

[22] Filed: May 14, 1979

[30] Foreign Application Priority Data

May 15, 1978 [JP] Japan .................. 53-58021
Feb. 8, 1979 [JP] Japan .................. 54-14516
Feb. 8, 1979 [JP] Japan .................. 54-14517

[51] Int. Cl.$^3$ .................. A01N 57/28; C07F 9/28; C07D 277/66; C07D 417/02
[52] U.S. Cl. .................. 424/200; 546/21; 548/113
[58] Field of Search .................. 546/21; 260/304 P; 424/200; 548/113

[56] References Cited

U.S. PATENT DOCUMENTS 3,897,442  7/1975  Edwards .................. 424/200

OTHER PUBLICATIONS

Arzneimittel-Forschung, 22, p. 22 (1972), (I).
Arzneimittel-Forschung, 22, p. 1 (1972), (II).
Arzneimittel-Forschung, 21, p. 1338 (1971).
Arzneimittel-Forschung, 27, p. 878 (1977).
Arzneimittel-Forschung, 20, p. 1310 (1970).

*Primary Examiner*—John M. Ford
*Assistant Examiner*—Robert C. Whittenbaugh
*Attorney, Agent, or Firm*—Haight, Rosfeld, Noble & Santa Maria

[57] ABSTRACT

A phosphonic acid ester of the formula:

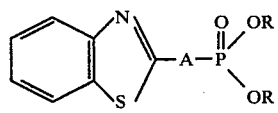

wherein A is and R is a lower alkyl, exhibits a calcium-antagonistic activity. Pharmaceutical compositions containing the same are useful in prophylaxis and treatment of ischemic heart diseases such as angina pectoris, myocardial, infarction, etc. and hypertension.

12 Claims, No Drawings

CALCIUM-ANTAGONISTIC COMPOSITION

This invention relates to a novel calcium-antagonistic pharmaceutical composition which is useful in the prophylaxis and treatment of ischemic heart diseases such as angina pectoris, myocardial infarction, etc. and hypertension.

The 'calcium antagonist' is a name coined by Freckenstein [Calcium and the Heart, ed. P. Harris and L. Oie, Academic Press, P. 135 (1971)] to designate substances which through competitive antagonism against Ca ions inhibit the contraction of smooth muscles, heart muscles, etc. Among the compounds hitherto-known as calcium antagonists are nifedipine, verapamil, diltiazem, prenylamine etc. [For details of the calcium antagonism actions of these compounds, reference may be made to Arzneimittel-Forschung, 22: p. 22 (1972), The Japanese Journal of Pharmacology, 25: p. 383 (1975) and Pflügers Archiv., 307: R 25 (1969).]

These compounds have been found to have strong coronary vasodilator activity [e.g. Arzneimittel-Forschung, 21: 1338 (1971) and Arzneimittel-Forschung, 22: 1 (1972)] and their utility has been established by clinical trials [e.g. Shinzo, 3, 1325 (1971), Medizinische Welt, 26: 1847 (1975), Post-Graduate Medical Journal, 52: 143 (1976), British Heart Journal, 36: 1001 (1974) and Arzneimittel Forschung, 27: 878 (1977)], while the usefulness of the compounds as hypotensive drugs has also been suggested [e.g. Japanese Heart Journal, 15: 128 (1972), Japanese Heart Journal, 17: 479 (1976), Arzneimittel-Forschung, 20: 1310 (1970), Shinryo-to-Shinyaku, 14: 761 (1977) and Rinsho-to Kenkyu, 54: 241 (1977)]

As is apparent from a reading of the above literature, calcium antagonists are drugs which are of great clinical use in the treatment of circulatory organ diseases, particularly angina pectoris and hyptetension.

As it is, the known calcium antagonists are disadvantageous in that they are comparatively high in toxicity, chemically unstable and not very strong in calcium antagonistic activity.

It has now been surprisingly discovered that 2-(benzothiazol-2-yl)-5-di-lower alkoxyphosphinylmethyl-pyridines or 1-(benzothiazol-2-yl)-4-di-lower alkoxyphosphinylmethylbenzenes exhibit a marked calcium antagonist activity with less toxicity compared with the known calcium antagonists and, therefore, they are useful in the prophylaxis and treatment of ischemic heart diseases such as angina pectoris, myocardial infarction, etc. and hypertension.

The above phosphonates have been known as starting materials for the synthesis of fluorescent whiteners (cf. Japanese Laid-Open Patent No. 314/74 and U.S. Pat. No. (3,586,673) but their biological or pharmaceutical properties have not been investigated.

Accordingly, the present invention is directed to a calcium-antagonistic pharmaceutical composition comprising a therapeutically effective amount of a phosphonate of the formula:

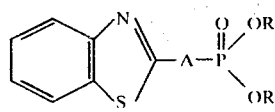

wherein A is

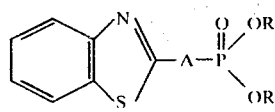 —CH₂— or 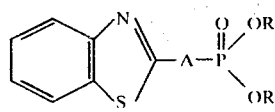 —CH₂— and R is a lower alkyl, in combination with a pharmaceutically acceptable, non-toxic inert carrier.

The term "lower alkyl" used herein stands for alkyl groups of $C_1$–$C_4$.

Examples of said phosphonates include: 2-(benzothiazol-2-yl)-5-dimethoxyphosphinylmethyl-pyridine; 2-(benzothiazol-2-yl)-5-diethoxyphosphinyl-methylpyridine; 2-(benzothiazol-2-yl)-5-di-n-propyloxyphosphinylmethylpyridine; 2-(benzothiazol-2-yl)-5-di-iso-propyloxyphosphinylmethylpyridine; 2-(benzothiazol-2-yl)-5-di-n-butyloxyphosphinylmethylpyridine; 1-(benzothiazol-2-yl)-4-dimethoxyphosphinylmethyl-benzene; 1-(benzothiazol-2-yl)-4-diethoxyphosphinyl-methylbenzene; 1-(benzothiazol-2-yl)-4-di-n-propyloxyphosphinylmethylbenzene; 1-(benzothiazol-2-yl)-4-di-iso-propyloxyphosphinylmethylbenzene; and 1-(benzothiazol-2-yl)-4-di-n-butyloxyphosphinylmethylbenzene.

The effectiveness of the above phosphonic esters will now be shown by way of test in laboratory animals.

1. Calcium antagonist activity

Male guinea-pigs weighing 350–450 g each were slaughtered and a test was conducted using isolated taenia colis about 2 cm long. A taenia coli was suspended in a Magnus chamber (Locke solution, 25°±2° C., aerated) and the contractile response of the taenia coli was recodered through an isotonic transducer. To the decalcified taenia coli was cumulatively added 0.1 to 100 mM of calcium in the presence of $6 \times 10^{-3}$ g/ml of $K^+$ to obtain a dose-contraction curve for calcium and, after the taenia coli was decalcified again, a dose-contraction curve for calcium was determined in the presence of the test compound. Based on the difference between the responses, the $pA_2$ of calcium antagonist activity of the test compound was computed. Table 1 shows the calcium antagonist activities ($pA_2$) of the compounds tested.

TABLE 1

| Compound and Concentration | No. of cases | $pA_2$ (mean ± standard error) values |
|---|---|---|
| 2-(Benzothiazol-2-yl)-5-di-iso-propyloxyphosphinyl-methylpyridine $1 \times 10^{-6}$ g/ml | 5 | 5.59 ± 0.11 |
| 2-(Benzothiazol-2-yl)-5-di-n-propyloxyphosphinyl-methylpyridine $1 \times 10^{-6}$ g/ml | 5 | 5.95 ± 0.09 |
| 2-(Benzothiazol-2-yl)-5-di-n-butyloxyphosphinyl-methylpyridine $1 \times 10^{-6}$ g/ml | 5 | 5.39 ± 0.15 |
| 2-(Benzothiazol-2-yl)-5-diethoxyphosphinylmethyl-pyridine $3 \times 10^{-8}$ g/ml | 5 | 7.43 ± 0.11 |
| 1-(Benzothiazol-2-yl)-4-diethoxyphosphinylmethyl-benzene $3 \times 10^{-8}$ g/ml | 5 | 6.92 ± 0.28 |
| 1-(Benzothiazol-2-yl)-4-di-iso-propyloxyphosphinyl-methylbenzene $3 \times 10^{-6}$ g/ml | 5 | 6.11 ± 0.07 |
| Diltiazem | | |

TABLE 1-continued

| Compound and Concentration | No. of cases | pA$_2$ (mean ± standard error) values |
|---|---|---|
| 1 × 10$^{-7}$ g/ml | 5 | 6.38 ± 0.12 |

2. Action on the cardiovascular system (1) Action on the isolated guinea-pig heart Male guinea-pigs with body weights from 400 to 500 g were slaughtered and promptly thoractomized. After the ascending aorta was cannulated, the heart was enucleated. By the method of Langendorff, this isolated heart was perfused with the Krebs-Henseleit fluid oxygenated with a gaseous mixture of 95% O$_2$ and 5% CO$_2$ at a fluid temperature of 34° ± 1° C. and perfusion pressure of 60 cm H$_2$O, and the the test compound was infused. The coronary flows before and after infusion were measured and the percent gain in coronary flow was obtained. The coronary flow was measured with a square-wave electromagnetic flowmeter (Nihon Kohden, MF-26) with an extracorporeal probe (Nihon Kohden, FE) set at the top of the cannula and recorded with a multipurpose polygraph (Nihon Kohden, RM-85). The test compound was dissolved in propylene glycol to a concentration of 100 γ/ml and 0.1 ml of the solution was infused at the rate of 0.1 ml/min. The results are shown in Table 2. For reference, the corresponding data on diltiazem is also shown.

TABLE 2

Action on Coronary Blood Flow

| Compound | No. of cases | Dosage (γ/heart) | Maximum increase in coronary flow (Δ% ± standard error) |
|---|---|---|---|
| 2-(Benzothiazol-2-yl)-5-dimethoxyphosphinylmethylpyridine | 4 | 10 | 28.6 ± 3.8 |
| 2-(Benzothiazol-2-yl)-5-di-n-propyloxyphosphinylmethylpyridine | 3 | 10 | 66.0 ± 21.6 |
| 2-(Benzothiazol-2-yl)-5-di-iso-propyloxyphosphinylmethylpyridine | 3 | 10 | 79.9 ± 13.1 |
| 2-(Benzothiazol-2-yl)-5-di-n-butyloxyphosphinylmethylpyridine | 4 | 10 | 50.3 ± 10.8 |
| 2-(Benzothiazol-2-yl)-5-diethoxyphosphinylmethylpyridine | 16 | 10 | 98.6 ± 10.6 |
| 1-(Benzothiazol-2-yl)-4-dimethylphosphinylmethylbenzene | 4 | 10 | 38.5 ± 13.6 |
| 1-(Benzothiazol-2-yl)-4-diethoxyphosphinylmethylbenzene | 7 | 10 | 83.8 ± 9.0 |
| 1-(Benzothiazol-2-yl)-4-di-n-propyloxyphosphinylmethylbenzene | 7 | 10 | 65.1 ± 12.2 |
| 1-(Benzothiazol-2-yl)-4-di-iso-propyloxyphosphinylmethylbenzene | 4 | 10 | 90.7 ± 31.7 |
| 1-(Benzothiazol-2-yl)-4-di-n-butyloxyphosphinylmethylbenzene | 4 | 10 | 65.1 ± 22.8 |
| Diltiazem | 13 | 10 | 66.0 ± 7.1 |

(2) Action on coronary flow and blood pressure (intraveous administration into dogs)

Dogs weighing 11 to 24 kg were anaesthetized with pentobarbital sodium (35 mg/kg, intraperitoneal) and, under supportive respiration, a right thoractomy was performed by removing the fourth rib. The pericardial membrane was then incised to expose the heart. The coronary sinus flow was measured with a cannula inserted from the right auricle into the coronary sinus and connected to an electromagnetic flowmeter (Nihon Kohden K.K., MF-26.) The outflowing blood was returned to the femoral vein through a rubber tubing.

The blood pressure was measured with a pressure transducer (Nihon Kohden K.K., MPU-0.5) connected to the cannula inserted into the femoral artery, and was recorded with a multipurpose polygraph (Nihon Kohden K.K., RM-85) which also recorded the coronary blood flow. The heart rate was calculated based on the electrocardiogram. The test compound was dissolved in dog serum and injected into the femoral vein.

The results are shown in Table 3.

TABLE 3

Coronary flow increasing action, and hypotensive action (dogs, intravenous administration)

| Compound | Dosage (mg/kg) | No. of cases | Increase in coronary senus outflow (Δ% ± standard error) | Mean change in blood pressure (ΔmmHg ± standard error) | Change in heart rate (Δbeats/min. ± standard error) |
|---|---|---|---|---|---|
| 2-(Benzothiazol-2-yl)-5-diethoxyphosphinylmethylpyridine | 0.2 | 6 | 74.4 ± 7.3 | −14.5 ± 5.4 | −16.3 ± 3.2 |
| 1-(Benzothiazol-2-yl)-4-diethoxyphosphinylmethylbenzene | 0.2 | 5 | 42.8 ± 6.2 | −10.0 ± 3.6 | −11.2 ± 2.1 |
| Diltiazem (control) | 0.2 | 6 | 67.9 ± 8.5 | −21.4 ± 6.1 | −20.5 ± 7.8 |

(3) Activity on intraduodenal administration to dogs

Dogs weighing 12 to 22 kg were anaesthetized with pentobarbital sodium [35 mg/kg, i.p.] and under supportive respiration, a left thoractomy was performed at the fourth interspace. The pericardium was incised to expose the heart and the blood flow through circumflex branch of left coronary was measured with an electromagnetic flowmeter (Nihon Kohden K.K., MF-26). The blood pressure was measured from a cannula inserted into the carotid artery through a pressure transducer (Nihon Kohden K.K., MPU-0.5), while the heart rate was calculated based on the electrocardiogram. The abdomen was sutured with the end of the cannula left out of the body and the test compound was administered. The test compound was diluted with 0.5% CMC to a concentraion of 10 mg/ml and administered at a dose of 10 mg/kg.

Table 4 shows the results.

TABLE 4

Coronary flow increasing action and hypotensive action (dogs, intraduodenal administration, 10 mg/kg)

| Compound | No. of cases | Time after administration | Increase in blood flow through circumflex branch of left coronary ($\Delta\%$ ± standard error) | Mean change in blood flow ($\Delta$mmHg ± standard error) | Change in heart rate ($\Delta$beats/min. ± standard error) |
|---|---|---|---|---|---|
| 2-(Benzothiazol-2-yl)-diethoxy-phosphinyl-methylpyridine | 7 | 5<br>30<br>60<br>120 | 14.3 ± 7.4<br>37.7 ± 9.6<br>54.4 ± 11.3<br>50.7 ± 12.7 | −12.9 ± 3.4<br>−12.4 ± 2.3<br>−11.0 ± 3.5<br>−11.2 ± 3.9 | −5.6 ± 1.2<br>−23.3 ± 3.8<br>−26.9 ± 3.8<br>−26.4 ± 3.8 |
| Diltiazem | 5 | 5<br>30<br>60<br>120 | 1.8 ± 1.8<br>34.4 ± 8.2<br>33.0 ± 12.2<br>34.8 ± 15.1 | −2.4 ± 1.3<br>−11.0 ± 1.3<br>−14.4 ± 2.3<br>−16.0 ± 4.7 | 1.6 ± 2.0<br>−13.2 ± 1.2<br>−23.0 ± 2.5<br>−23.6 ± 4.0 |

3. Acute toxicity test

An acute toxicity test was performed in male ddY mice (in groups of 5 animals, body weights 20±2 g) by the intraperitoneal administration of a test compound.

A suspension of each compound in 0.5% carboxymethylcellulose was administered, the deaths within 72 hours were counted and the $LD_{50}$ values were calculated by the method of Weil. The results are given in Table 5.

TABLE 5

| Acute toxicity in mice, introperitoneal | |
|---|---|
| Compound | $LD_{50}$(mg/kg) |
| 2-(Benzothiazol-2-yl)-5-di-n-propyloxyphosphinylmethylpyridine | 713 |
| 2-(Benzothiazol-2-yl)-5-di-iso-propyloxyphosphinylmethylpyridine | >2250 |
| 2-(Benzothiazol-2-71))-5-diethoxy-phosphinylmethylpyridine | 1062 |
| 1-(Benzothiazol-2-yl)-4-dimethoxy-phosphinylmethylbenzene | 1070 |
| 1-(Benzothiazol-2-yl)-4-diethoxy-phosphinylmethylbenzene | 962 |
| 1-(Benzothiazol-2-yl)-4-di-n-propyl-oxyphosphinylmethylbenzene | >2250 |
| 1-(Benzothiazol-2-yl)-4-di-iso-propyl-oxyphosphinylmethylbenzene | 1660 |
| 1-(Benzothiazol-2-yl)-4-di-n-butyl-oxyphosphinylmethylbenzene | >2250 |

It will be apparent from the above results that the active compounds according to this invention are at least equivalent to the control drug diltiazem in calcium antagonism and coronary flow increasing activity, with by far lower toxicity.

The pharmaceutical composition of this invention can be easily prepared by applying established pharmaceutical procedures to the active compound.

Thus, an oral preparation, for instance, can be produced in the following manner. The compound, together with a pharmacologically acceptable carrier or excipient, e.g. lactose, starch, crystalline cellulose, kaolin, calcium carbonate or talc, is formed into tablets, granules, pellets or powders by established pharmaceutical procedures. Alternatively, the compound can be suspended in an aqueous solution of carboxymethylcellulose, gum arabic or the like to make a syrup. It is also possible to prepare an injectable solution by dissolving the compound alone or together with a nonionic surfactant, such as polyoxyethylene—castor oil, in water. The compound may also be made into a suppository as formulated with a vegetable saturated fatty acid glyceride such as theobroma oil in the per se conventional manner.

While the proper relative amount of the active compound in such a preparation varies with different dosage forms, an oral dosage form, for instance, may normally contain the active compound in such an amount as will dose the subject with 1 mg to 5 mg/kg/day, whether an antianginal effect is expected or an antihypertensive effect is desired.

Although the clinical dosage should vary with the condition of the patient, a generally satisfactory oral regimen may thus be 50 to 250 mg daily and, for still better results, 50 to 100 mg daily for an adult weighing 50 kg, to be given in 3 divided doses daily.

The following production and working examples are given only to illustrate this invention in further detail and should by no means be construed as limiting the scope of the invention.

EXAMPLE 1

Synthesis of 2-(benzothiazole-2-yl)-5-dimethoxyphosphinylmethylpyridine

Synthesis of 2-(benzothiazol-2-yl)-5-methylpyridine 22.5 g (0.18 mol) of o-aminothiophenol, 25 g (0.18 mol) of 5-methylpicolic acid and 100 g of polyphosphoric acid were admixed and stirred in nitrogen gas streams at 170°–200° C. and the mixture was poured in 1 l of water. The mixture was adjusted to pH 5 with an aqueous solution of sodium hydroxide and the resulting crystals were recovered by filtration, whereupon 40 g of 2-(benzothiazol-2-yl)-5methylpyridine was obtained as crude crystals. This crude product was recrystallized from ligroine. By the above procedure was obtained 36 g of the same compound as colorless flakes melting at 169.5°–170.0° C.

Synthesis of 2-(benzothiazol-2-yl)-5-bromomethylpyridine

In 800 ml of dry carbon tetrachloride was dissolved 20 g (0.088 mol) of 2-(benzothiazol-2-yl)-5-methylpyridine, followed by the addition of 16.4 g (0.092 mol) of N-bromosuccinimide and a catalytic amount of benzoyl peroxide. The mixture was heated at reflux for 10 hours, after which time it was allowed to cool down to room temperature. The precipitated succinimide was filtered off, the filtrate concentrated to 200 ml and the resulting crude crystals collected by filtration. Yield 24 g. Recrystallization from ligroine yielded 19 g of 2-(benzothiazol-2-yl)-5-bromomethylpyridine as colorless needles.

Synthesis of 2-(benzothiazol-2-yl)-5-dimethoxyphpsphinylmethylpyridine 1.5 g (0.0049 mol) of 2-(benzothiazol-2-yl)-5-bromomethylpyridine was reacted with 3 ml of trimethyl phosphite in nitrogen gas streams at 130°–160° C. for 15 minutes. The reaction mixture was allowed to cool down to room temperature and the resulting crystals were recrystallized from ethyl acetate. By the above procedure was obtained 1.1 g (70%) of 2-(benzothiazol-2-yl)-5-dimethoxyphosphinylmethylpyridine as colorless needles, m.p. 151.5°–152.5° C.

EXAMPLES 2 TO 5

The compounds given in Table 6 were synthesized by reacting 2-(benzothiazol-2-yl)-5-bromomethylpyridine with the corresponding trialkyl phosphite in the same manner as Example 1.

TABLE 6

| Compound | | Yield (%) | Crystal form | m.p. (°C.) (recryst. solvent) |
|---|---|---|---|---|
| Ex. 2 | 2-(Benzothiazol-2-yl)-5-di-n-propyloxyphosphinylmethylpyridine | 74 | Colorless flakes | 113.0–115.0 (cylclohexane) |
| Ex. 3 | 2-(Benzothiazol-2-yl)-5-di-iso-propyloxyphosphinylmethylpyridine | 75 | Colorless needles | 125.0–127.0 (n-hexane) |
| Ex. 4 | 2-(Benzothiazol-2-yl)-5-di-n-butyloxyphosphinylmethylpyridine | 80 | Colorless needles | 106.5–107.5 (n-hexane) |
| Ex. 5 | 2-(Benzothiazol-2-yl)-5-diethoxyphosphinylpyridine | 77 | Colorless needles | 96.0–96.5 (n-hexane) |

EXAMPLE 6

Synthesis of 1-(benzothiazol-2-yl)-4-dimethoxyphoshinylmethylbenzene

Synthesis of 4-(benzothiazol-2-yl) toluene 125 g (1 mol) of o-aminothiophenol, 136 g (1 mol) of p-toluic acid and 600 g of polyphosphoric acid were admixed and stirred into nitrogen gas at 170°–200° C. for 4 hours. After the reaction mixture was cooled to 100° C., it was poured in 5 l of water. The mixture was adjusted to pH 5 with NaOH and the resulting crystals were filtered off, whereupon 220 g of 4-(benzothiazol-2-yl) toluene was obtained as crude crystals. Recrystallization from n-hexane gave 172 g of pure product as colorless prisms melting at 84°–85° C.

Synthesis of 4-(benzothiazol-2-yl) bromomethylbenzene

To a solution of 45 g (0.2 mol) of 4-(benzothiazol-2-yl) toluene in 1000 ml of dry carbon tetrachloride were added 35.6 g (0.2 mol) of N-bromosuccinimide and a catalytic amount of benzoyl peroxide. The mixture was refluxed for 12 hours, and then allowed to cool down to room temperature. The precipitated succinimide was filtered off and the filtrate evaporated to dryness in vacuo, whereupon 55 g of crude crystals were obtained. Recrystallization from 1500 ml of cyclohexane gave 41 g of purified 4-(benzothiazol-2-yl) bromomethylbenzene as colorless flakes.

Synthesis of 1-(benzothiazol-2-yl)-4-dimethoxyphosphinylmethylbenzene 6.08 g (0.2 mol) of 4-(benzothiazol-2-yl) bromomethylbenzene was reacted with 10 ml of trimethyl phosphite in nitrogen gas at 130°–160° C. for 15 minutes. The reaction mixture was allowed to cool down to room temperature and the resulting crystals were crystallized from n-hexane to give 3.9 g (83%) of colorless flakes of 1-(benzothiazol-2-yl)-4-dimethoxyphosphinylmethylbenzene melting at 129.5°–130.5° C.

EXAMPLES 7 TO 10

The compounds given in Table 6 were synthesized by reacting 1-(benzothiazol-2-yl) bromomethylbenzene with the corresponding trialkyl phosphite in the same manner as Example 7.

TABLE 7

| | Compound | Yield | Crystal form | m.p. °C. (recryst. solvent) |
|---|---|---|---|---|
| Ex. 7 | 1-(Benzothiazol-2-yl)-4-diethoxyphosphinylmethylbenzene | 92 | Colorless needles | 96.0–97.0 (n-hexane) |
| Ex. 8 | 1-(Benzothiazol-2-yl)-4-di-n-propyloxyphosphinylmethylbenzene | 93 | Colorless needles | 108.0–108.5 (n-hexane) |
| Ex.9 | 1-(Benzothiazol-2-yl)-4-di-iso-propyloxyphosphinylmethylbenzene | 75 | Colorless flakes | 121.0–122.0 (n-hexane) |
| Ex. 10 | 1-(Benzothiazol-2-yl)-4-di-n-butyloxyphosphinylmethylbenzene | 81 | Colorless needles | 105.5–106.5 (n-hexane) |

EXAMPLE 11—Tablets

| Components | Wt. Parts |
| --- | --- |
| 2-(Benzothiazol-2-yl)-5-diethoxyphosphinylmethylpyridine | 30 |
| Lactose | 90 |
| Corn starch | 36 |
| Magnesium stearate | 4 |

Procedure: 2-(Benzothiazol-2-yl)-5-diethoxyphosphinylmethylpyridine, lactose and corn starch were admixed in the above proportions and the mixture was kneaded to prepare granules. After drying, the granules were mixed with magnesium stearate and the composition was tableted to prepare tablets weighing 160 mg. each.

EXAMPLE 12—Capsules

The same components as used in Example 11 were taken in the same proportions and 160 mg portions of the mixture were dispensed into #4 hard gelatin capsules.

EXAMPLE 13—Granules

| Components | Wt. Parts |
| --- | --- |
| 2-(Benzothiazol-2-yl)-5-diethoxyphosphinylmethylpyridine | 60 |
| Mannitol | 640 |
| Lactose | 290 |
| Hydroxypropylcellulose | 10 |

Procedure: 2-(Benzothiazol-2-yl)-5-diethoxyphosphinylmethylpyridine, mannitol and lactose were admixed in the above proportions and the mixture was kneaded with an aqueous solution of hydroxypropylcellulose. The composition was then kneaded and dried, whereby granules were obtained.

EXAMPLE 14—Syrup

| Components | Amounts |
| --- | --- |
| 2-(Benzothiazol-2-yl)-5-diethoxyphosphinylmethylpyridine | 1 g |
| Methylcellulose | 0.5 g |
| Sucrose | 20 g |
| Methylparaben | 0.05 g |
| Propylparaben | 0.05 g |
| Strawberry essence | 0.01 g. |

Procedure: The above components were added in the indicated order and made up with distilled water to 100 ml. By the above procedure was obtained a syrup containing 10 mg of 2-(benzothiazol-2-yl)-5-di-ethoxyphosphinylmethylpyridine per ml.

EXAMPLE 15—Suppositories

| Components | Grams per suppository |
| --- | --- |
| 2-(Benzothiazol-2-yl)-5-diethoxyphosphinylmethylpyridine | 0.05 g |
| Theobrama oil | 1.5 g |

Procedure: The above components were admixed under heating and the mixture was molded in PVC suppository containers.

EXAMPLE 16 TO 20

Examples 11 to 15 were repeated except that 1-(benzothiazol-2-yl)-4-diethylphosphinylmethylbenzene was substituted for 2-(benzothiazol-2-yl)-5-diethoxyphosphinylmethylpyridine.

The above has been offered for illustrative purposes only, and is not intended to limit the scope of the invention of this application, which is as defined in the claims below.

We claim:

1. A calcium-antagonistic pharmaceutical composition comprising a therapeutically effective amount of a phosphonate of the formula:

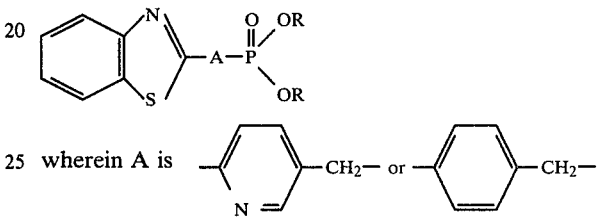

wherein A is and R is $C_1-C_4$ alkyl, in combination with a pharmaceutically acceptable, non-toxic inert carrier.

2. The composition according to claim 1, wherein said phosphonate is 2-(benzothiazol-2-yl)-5-dimethoxyphosphinylmethylpyridine.

3. The composition according to claim 1, wherein said phosphonate is 2-(benzothiazol-2-yl)-5-diethoxyphosphinylmethylpyridine.

4. The composition according to claim 1, wherein said phosphonate is 2-(benzothiazol-2-yl)-5-di-n-propyloxyphosphinylmethylpyridine.

5. The composition according to claim 1, wherein said phosphonate is 2-(benzothiazol-2-yl)-5-di-iso-propyloxyphosphinylmethylpyridine.

6. The composition according to claim 1, wherein said phosphonate is 2-(benzothiazol-2-yl)-5-di-n-butyloxyphosphinylmethylpyridine.

7. The composition according to claim 1, wherein said phosphonate is 1-(benzothiazol-2-yl)-4-dimethoxyphosphinylmethylbenzene.

8. The composition according to claim 1, wherein said phosphonate is 1-(benzothiazol-2-yl)-4-diethoxyphosphinylmethylbenzene.

9. The composition according to claim 1, wherein said phosphonate is 1-(benzothiazol-2-yl)-4-di-iso-propyloxyphosphinylmethylbenzene.

10. The composition according to claim 1, wherein said phosphonate is 1-(benzothiazol-2-yl)-4-di-n-propyloxyphosphinylmethylbenzene.

11. The composition according to claim 1, wherein said phosphonate is 1-(benzothiazol-2-yl)-4-di-n-butyloxyphosphinylmethylbenzene.

12. A method for inducing calcium antagonist activity in the prophylaxis or treatment of ischemic heart disease, which comprises administering a safe and effective amount of a phosphonate according to claim 1 to a living animal.

* * * * *